United States Patent [19]

Widdig et al.

[11] 3,972,905
[45] Aug. 3, 1976

[54] QUINONEMONOXIME-ARYLACYLHYDRAZONES

[75] Inventors: Arno Widdig, Blecher, Germany; Ewald Urbschat, deceased, late of Cologne, Germany, by Gertrud Emma Maria Gerda Urbschat, heiress, Cologne, Germany; Ferdinand Grewe, Burscheid; Helmut Kaspers, Leverkusen, both of Germany

[73] Assignee: Bayer Aktiengesellschaft, Leverkusen, Germany

[22] Filed: Feb. 27, 1975

[21] Appl. No.: 553,874

[30] Foreign Application Priority Data

Mar. 4, 1974 Germany............................ 2410184

[52] U.S. Cl............................. 260/396 N; 424/324
[51] Int. Cl.²................ C07C 131/00; C07C 149/42
[58] Field of Search................................ 260/396 N

[56] References Cited
UNITED STATES PATENTS 2,785,101    3/1957    Urbschat et al. .................. 424/291

*Primary Examiner*—Vivian Garner
*Attorney, Agent, or Firm*—Burgess, Dinklage & Sprung

[57] ABSTRACT

Quinonemonoxime-arylacylhydrazones of the formula

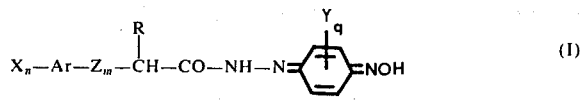

in which
  each X independently is halogen, nitro, $C_1$–$C_6$ alkyl or $C_1$–$C_6$ alkoxy,
  Ar is phenyl or naphthyl,
  Z is oxygen or sulfur,
  R is hydrogen, $C_1$–$C_6$ alkyl, hydroxyl or $C_1$–$C_6$ alkoxy,
  each Y independently is $C_1$–$C_6$ alkyl,
  $n$ is 0, 1, 2, 3 or 4,
  $m$ is 0 or 1, and
  $q$ is 0, 1 or 2
which possess fungicidal properties.

2 Claims, No Drawings

QUINONEMONOXIME-ARYLACYLHYDRAZONES

The present invention relates to and has for its objects the provision of particular new quinonemonoxime-arylacylhydrazones which possess fungicidal properties, active compositions in the form of mixtures of such compounds with solid and liquid dispersible carrier vehicles, and methods for producing such compounds and for using such compounds in a new way especially for combating pests, e.g., fungi, with other and further objects becoming apparent from a study of the within specification and accompanying examples.

Quinonoxime-acylhydrazones with fungicidal properties have already been disclosed in German Patent Specification 1,001,854. However, their action is not satisfactory. Thus, for example, the pathogens responsible for wilt diseases cannot be adequately combated.

The present invention provides, as new compounds, the quinonoxime-acylhydrazone derivatives of the general formula

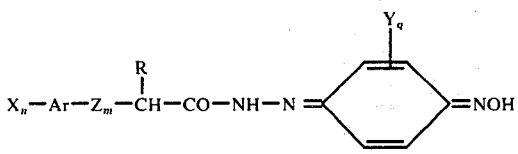

in which
each X independently is halogen, nitro, $C_1$–$C_6$ alkyl or $C_1$–$C_6$ alkoxy,
Ar is phenyl or naphthyl,
Z is oxygen or sulfur,
R is hydrogen, $C_1$–$C_6$ alkyl, hydroxyl or $C_1$–$C_6$ alkoxy,
each Y independently is $C_1$–$C_6$ alkyl,
$n$ is 0, 1, 2, 3 or 4,
$m$ is 0 or 1, and
$q$ is 0, 1 or 2

Preferably X is chlorine, bromine, methoxy, nitro or alkyl with up to 4 carbon atoms, ethyl, isopropyl or t.-butyl, R is hydrogen, hydroxyl, methyl, ethyl or methoxy, $n$ is 0, 1, 2 or 3, Y is methyl and $q$ is 0 or 1.

It is distinctly surprising that the quinonoxime-acylhydrazone derivatives according to the invention display an improved fungicidal activity as compared to the above-mentioned quinonoxime-acylhydrazones of the prior art. The active compounds according to the invention thus represent a valuable enrichment of the art. At the same time it should be emphasized that by using the compounds according to the invention it is also possible-as will be explained in more detail-to deal with the wilt diseases which are relatively difficult to combat.

The invention also provides a process for the preparation of a quinonoxime-acylhydrazone derivative of the formula (I) in which an acylhydrazide of the general formula

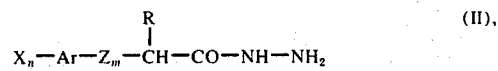

in which
X, Ar, Z, R, $n$ and $m$ have the above-mentioned meanings, is reacted with a quinonemonoxime (identical to the corresponding nitrosophenol) of the general formula

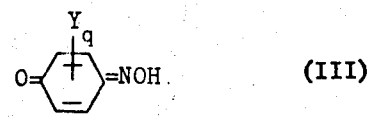

in which
Y and $q$ have the above-mentioned meanings, in the presence of a diluent and of at least an equivalent amount of mineral acid, in the temperature range of about 0° to 100°C.

If naphthyl-1-acetic acid hydrazide and quinonemonoxime are used as starting materials, the course of the reaction can be represented by the following equation:

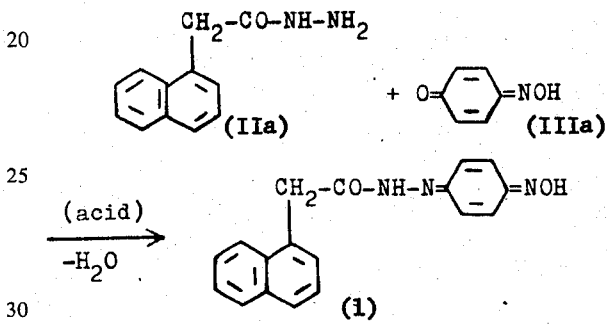

The following may be mentioned as examples of the hydrazides: phenylacetic acid hydrazide, phenoxyacetic acid hydrazide, 2-chlorophenoxyacetic acid hydrazide, 2,4-dichlorophenoxyacetic acid hydrazide, 2,4,5-trichlorophenoxyacetic acid hydrazide, 2,4,6-trichlorophenoxyacetic acid hydrazide, 4-chlorophenoxyacetic acid hydrazide, 4-bromophenoxyacetic acid hydrazide, 2-methylphenoxyacetic acid hydrazide, 3-methylphenoxyacetic acid hydrazide, 4-methylphenoxyacetic acid hydrazide, 2-methyl-4-chloro-phenoxyacetic acid hydrazide, 3,5-dimethyl-4-chloro-phenoxyacetic acid hydrazide, 2-chloro-4-methyl-phenoxyacetic acid hydrazide, 4-nitro-phenoxyacetic acid hydrazide, 2-nitro-phenoxyacetic acid hydrazide, 2-methoxy-phenoxyacetic acid hydrazide, 3-methoxyphenoxyacetic acid hydrazide, 4-methoxyphenoxyacetic acid hydrazide, phenylmercaptoacetic acid hydrazide, 2-chlorophenylmercaptoacetic acid hydrazide, 4-chlorophenylmercaptoacetic acid hydrazide, 3,4-dichlorophenylmercaptoacetic acid hydrazide, 2,4-dichlorophenylmercaptoacetic acid hydrazide, 2,4,5-trichlorophenylmercaptoacetic acid hydrazide, 2,4,6-trichlorophenylmercaptoacetic acid hydrazide, 2-bromo-phenylmercaptoacetic acid hydrazide, 4-bromo-phenylmercaptoacetic acid hydrazide, 2-methylphenylmercaptoacetic acid hydrazide, 3-methyl-phenylmercaptoacetic acid hydrazide, 4methyl-phenylmercaptoacetic acid hydrazide, 2,3-dimethyl-phenylmercaptoacetic acid hydrazide, 2,4-dimethyl-phenylmercaptoacetic acid hydrazide, 2,5-dimethylphenylmercaptoacetic acid hydrazide, 2-methyl-4-chloro-phenylmercaptoacetic acid hydrazide, 2-methyl-3-chloro-phenylmercaptoacetic acid hydrazide, 2-chloro-4 -methyl-phenylmercaptoacetic acid hydrazide, 2-chloro-3-methyl-phenylmercaptoacetic acid hydrazide, 2,4-dichloro-5-methyl-phenylmercaptoacetic acid hydrazide, 2-ethyl-phenylmercaptoacetic acid hydrazide, 4-ethyl-phenylmercaptoacetic acid hydrazide, 2-isopropyl-phenylmercaptoacetic acid hydrazide, 4-isopropyl-phenylmercaptoacetic acid hydrazide, 2-t.-butyl-phenylmercaptoacetic acid hydrazide, 4-t.-butyl-phenylmercaptoacetic acid hydrazide, 2-methoxy-phenylmercaptoacetic acid hydrazide, 3-methoxyphenylmercaptoacetic acid hydrazide, 4-methoxy-phenylmercaptoacetic acid hydrazide, 2-methoxy-4-chloro-phenylmercaptoacetic acid hydrazide, 2-nitro-phenylmercaptoacetic acid hydrazide, 4-nitro-phenylmercaptoacetic acid hydrazide, 2-chloro-4-nitrophenylmercaptoacetic acid hydrazide, 2-nitro-4-chloro-phenylmercaptoacetic acid hydrazide, 2,4-dinitro-phenylmercaptoacetic acid hydrazide, 2-nitro-4-methyl-phenylmercaptoacetic acid hydrazide, 2-methyl-4-nitro-phenylmercaptoacetic acid hydrazide, mandelic acid hydrazide, α-methoxyphenylacetic acid hydrazide, α-phenoxypropionic acid hydrazide, α-2,4-dichlorophenoxypropionic acid hydrazide, α-4-chlorophenoxypropionic acid hydrazide, α-phenylmercapto-propionic acid hydrazide, α-phenylmercapto-butyric acid hydrazide, α-4-chloro-phenylmercapto-propionic acid hydrazide, naphthyl-2-acetic acid hydrazide, naphthyl-1-acetic acid hydrazide, naphth-(1)-oxyacetic acid hydrazide, naphth-(2)-oxyacetic acid hydrazide, α-(naphth-(1)-oxy)-propionic acid hydrazide, α-(naphth-(2)-oxy)-propionic acid hydrazide, α-(naphth-(1)-oxy)-butyric acid hydrazide and α-(naphth-(2)-oxy)-butyric acid hydrazide.

Acylhydrazides of the formula (II) used as starting materials are known (*J. Amer. Chem. Soc.* Vol. 75, (1953) page 1933; *J. Chem. Soc.* (1953) page 1358; *J. Amer. Pharm. Assoc.* Vol. 42, (1953) page 402) and can easily be prepared from the corresponding esters by hydrazinolysis.

The following may be mentioned as examples of the quinonemonoximes which can be used according to the invention: quinonemonoxime (p-nitrosophenol), 2-methyl-quinonemonoxime (3-methyl-4-nitrosophenol) and 3-methyl-quinonemonoxime (2-methyl-4-nitrosophenol).

The quinonoximes (nitrosophenols) are known (see *Beilsteins Handbuch der organischen Chemie* (*Beilstein's Handbook of Organic Chemistry*), volume VII, pages 622, 647 et seq., Berlin (1925)).

Diluents which can be used when carrying out the process according to the invention are in the main water, the lower alcohols such as methanol, ethanol and isopropanol, and mixtures of these alcohols with water, in any desired ratios.

The reaction temperatures can be varied within a substantial range. In general, the reaction is carried out at between 0° and 100°C, preferably at between 10° and 60°C.

In carrying out the process according to the invention, 1.0 to 1.2 moles of the quinonemonoxime are employed per mole of hydrazide. It is possible to use up to 20% more or less without significant reduction in yield. The amount of acid added should be at least 1 equivalent but larger amounts can be employed without disadvantages.

The active compounds according to the invention have a strong fungitoxic action. Their low toxicity to warmblooded animals and their good toleration by higher plants permits their use as agents for protecting plants against fungal diseases. They do not harm crop plants in the concentrations required for combating the fungi. Fungitoxic agents are employed in plant protection for combating fungi from the most diverse categories of fungi, such as *Archimycetes*, *Phycomycetes*, *Ascomycetes*, *Basidiomycetes* and *Fungi Imperfecti*.

The active compounds according to the invention can be used against parasitary fungi on above-ground parts of plants, fungi causing tracheomycosis, which attack the plants through the soil, seed-borne fungi and fungi which inhabit the soil. They are particularly active against fungi which cause wilt diseases. This group of fungi predominantly includes representatives from the *fusarium* species and *verticillium* species.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, espcially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or nematocides, insecticides, acaricides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0005–0.05%, preferably 0.001–2%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g., a surface-active agent, such as an emulsifying agent and/or a dispersing agent, and an amount of the active compound which is effective for the purpose in question and which is generally between about 0.0005–95%, and preferably 0.001–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g., fungi, which comprises applying to at least one of correspondingly (a) such fungi, and (b) the corresponding habitat thereof, i.e., the locus to be protected, e.g., to a growing crop, to an area where a crop is to be grown or to a domestic animal, a correspondingly combative or toxic amount, i.e., a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Fusarium test/systemic

Solvent: 4.7 parts by weight of acetone
Dispersing agent: 0.3 part by weight of alkylaryl polyglycol ether
Water: 95 parts by weight The amount of active compound required for the desired concentration of active compound in the watering liquor was mixed with the stated amount of the solvent and the concentrate was diluted with the stated amount of water which contained the stated additive.

Tomato plants in the 2 to 3 leaf stage, in 400 cm$^3$ pots, were watered 5 times within one week with 50 ml of the watering liquor, in the stated active compound concentration, per 100 ml of soil. The plants thus treated were inoculated by dipping the roots into a spore suspension of *Fusarium oxysporum* f. sp. *lycopersici*. The inoculated plants were then planted in untreated soil and set up in a greenhouse with 80% atmospheric humidity at a temperature of 24°C.

3 Weeks after the inoculation, the infection was evaluated. 0% denotes no infection and 100% denotes total infection.

The active compounds, active-compound concentrations and results can be seen from the table which follows.

Table 1

| | Fusarium test/systemic | |
|---|---|---|
| | | Infection in % at an active compound concentration of |
| Active compound | 0.003% | 0.0015% |
| 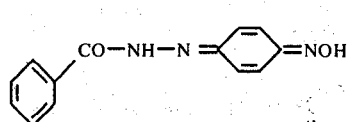 (known) (A) | 56 | 60 |
| 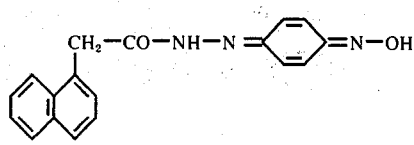 (1) | 0 | 0 |

Table 1-continued

| Active compound | Fusarium test/systemic | Infection in % at an active compound concentration of | |
|---|---|---|---|
| | | 0.003% | 0.0015% |
| Cl₃C₆H₂—O—CH₂—CO—NH—N=C₆H₄=NOH (2,4,6-trichlorophenoxy) | (6) | — | 0.4 |
| Cl—C₆H₄—S—CH₂—CO—NH—N=C₆H₄=NOH | (14) | 2 | 12 |
| Naphthyl-CH₂—CO—NH—N=C₆H₃(CH₃)=NOH | (10) | 0 | 0 |
| Naphthyl-CH₂—CO—NH—N=C₆H₃(CH₃)=NOH | (11) | 6 | 17 |
| Naphthyl-O—CH₂—CO—NH—N=C₆H₄=NOH | (2) | 0 | 0 |
| 2,4-dichlorophenoxy-CH₂—CO—NH—N=C₆H₄=NOH | (4) | 0 | 0 |

The process of this invention is illustrated by the following preparative Example.

EXAMPLE 2

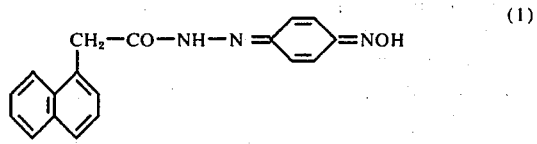

(1)

20 g (0.1 mole) of naphthyl-1-acetic acid hydrazide were dissolved in a mixture of 1.8 liters of water and 15 ml of concentrated hydrochloric acid, and a solution of 13.7 g (0.11 mole) of nitrosophenol in 100 ml of methanol was then added while cooling with ice. The mixture was stirred for a further 2 hours and left to stand overnight and the product which had precipitated was filtered off, washed with water, methanol and ether and dried in air. 22 g of a yellow crystal powder of melting point 213°C (with decomposition) were obtained. The yield was 72% of theory.

The following compounds were prepared similarly:

| Compound No. | Formula | Melting point (°C) |
|---|---|---|
| 2 | Naphthyl-2-O—CH₂—CO—NH—N=C₆H₄=NOH | 174 (decomposition) |
| 3 | C₆H₅—O—CH₂—CO—NH—N=C₆H₄=NOH | 187 (decomposition) |
| 4 | 2,4-dichlorophenyl-O—CH₂—CO—NH—N=C₆H₄=NOH | 202 (decomposition) |

-continued

| Compound No. | Formula | Melting point (°C) |
|---|---|---|
| 5 | 2,4,5-trichlorophenyl-O-CH₂-CO-NH-N=⟨⟩=NOH | 167 (decomposition) |
| 6 | 2,4,6-trichlorophenyl-O-CH₂-CO-NH-N=⟨⟩=NOH | 210 (decomposition) |
| 7 | 4-chloro-3,5-dimethylphenyl-O-CH₂-CO-NH-N=⟨⟩=NOH | 204 (decompositions) |
| 8 | C₆H₅-CH₂-CO-NH-N=⟨⟩=NOH | 182 (decomposition) |
| 9 | C₆H₅-CH(OCH₃)-CO-NH-N=⟨⟩=NOH | 100 |
| 10 | 1-naphthyl-CH₂-CO-NH-N=⟨CH₃⟩=NOH | 204 (decomposition) |
| 11 | 1-naphthyl-CH₂-CO-NH-N=⟨CH₃⟩=NOH | 192 (decomposition) |
| 12 | C₆H₅-O-CH₂-CO-NH-N=⟨⟩=NOH (with CH₃) | 200 (decomposition) |
| 13 | C₆H₅-S-CH₂-CO-NH-N=⟨⟩=NOH | 178 (decomposition) |
| 14 | 4-Cl-C₆H₄-S-CH₂-CO-NH-N=⟨⟩=NOH | 170 (decomposition) |
| 15 | 3,4-diCl-C₆H₃-S-CH₂-CO-NH-N=⟨⟩=NOH | 149 (decomposition) |
| 16 | C₆H₅-S-CH(CH₃)-CO-NH-N=⟨⟩=NOH | 156 (decomposition) |
| 17 | 2,4-diCl-C₆H₃-S-CH(C₂H₅)-CO-NH-N=⟨⟩=NOH | 162 (decomposition) |
| 18 | 2-Cl-4-O₂N-C₆H₃-S-CH₂-CO-NH-N=⟨⟩=NOH | 163 (decomposition) |
| 19 | 2-NO₂-4-Cl-C₆H₃-S-CH₂-CO-NH-N=⟨⟩=NOH | 176 (decomposition) |

| Compound No. | Formula | Melting point (°C) |
|---|---|---|
| 20 | 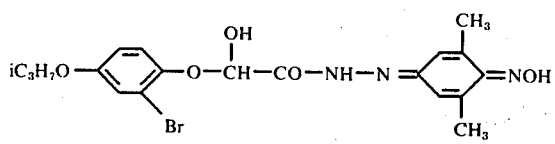 | 170 (decomposition) |

Other compounds which can also be similarly prepared include:

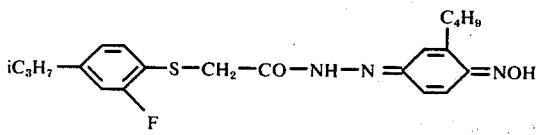

and the like.

It will be appreciated that the instant specification and examples are set forth by way of illustration and not limitation, and that various modifications and changes may be made without departing from the spirit and scope of the present invention.

What is claimed is:

1. The compound quinonemonoxime-2,4-dichlorophenoxy-acetic acid hydrazide of the formula

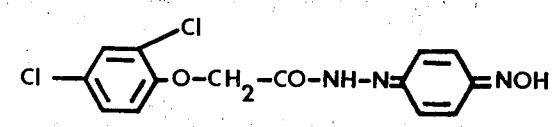

2. The compound quinonemonoxime-4-chlorophenyl-mercaptoacetic acid hydrazide of the formula

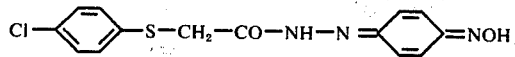

* * * * *